United States Patent
Salah et al.

(10) Patent No.: US 10,779,909 B2
(45) Date of Patent: Sep. 22, 2020

(54) METHOD FOR MONITORING AN ORTHODONTIC TREATMENT

(71) Applicant: DENTAL MONITORING, Paris (FR)

(72) Inventors: Philippe Salah, Bagnolet (FR); William Ayache, Neuilly-sur-Seine (FR); Laurent Debraux, Paris (FR); Guillaume Ghyselinck, Cantin (FR); Thomas Pellissard, Goussainville (FR)

(73) Assignee: DENTAL MONITORING, Paris (FR)

( * ) Notice: Subject to any disclaimer, the term of this patent is extended or adjusted under 35 U.S.C. 154(b) by 0 days.

(21) Appl. No.: 16/240,525

(22) Filed: Jan. 4, 2019

(65) Prior Publication Data

US 2019/0133717 A1    May 9, 2019

Related U.S. Application Data

(63) Continuation of application No. 15/522,606, filed as application No. PCT/EP2015/074859 on Oct. 27, 2015, now Pat. No. 10,206,759.

(30) Foreign Application Priority Data

Oct. 27, 2014   (FR) ..................... 14 60310

(51) Int. Cl.
*A61C 7/00* (2006.01)
*G06T 17/00* (2006.01)
(Continued)

(52) U.S. Cl.
CPC ............ *A61C 7/002* (2013.01); *A61B 5/0088* (2013.01); *A61B 5/064* (2013.01); *A61C 9/0053* (2013.01);
(Continued)

(58) Field of Classification Search
CPC ... A61C 7/002; A61C 9/0053; A61C 13/0004; A61C 19/066; A61C 19/10;
(Continued)

(56) References Cited

U.S. PATENT DOCUMENTS 5,278,756 A   1/1994  Lemchen et al.
6,328,567 B1  12/2001 Morris et al.
(Continued)

FOREIGN PATENT DOCUMENTS

CA   2292141 A1   6/2001
JP   5241971 B1   7/2013
(Continued)

OTHER PUBLICATIONS

Dec. 8, 2014 Search Report issued in International Patent Application No. PCT/IB2014/064658.
(Continued)

*Primary Examiner* — Brenda C Bernardi
(74) *Attorney, Agent, or Firm* — Oliff PLC

(57) ABSTRACT

A method including an acquisition, with an acquisition apparatus, of at least one two-dimensional image of arches of a patient, called "updated image", in actual acquisition conditions, a separator separating lips of the patient in order to improve the visibility of patient's teeth, said separator including a register mark, wherein the representation of the register mark on the updated image is used to recut the updated image and/or to roughly assess the actual acquisition conditions and/or to guide the positioning of the acquisition apparatus at the moment of the acquisition of the updated image and/or to identify a dental situation and/or an action to be achieved by the acquisition apparatus.

22 Claims, 5 Drawing Sheets

(51) Int. Cl.

| | | |
|---|---|---|
| *G06T 7/33* | (2017.01) | |
| *G06T 7/73* | (2017.01) | |
| *A61C 9/00* | (2006.01) | |
| *A61B 5/00* | (2006.01) | |
| *A61B 5/06* | (2006.01) | |
| *G06K 9/00* | (2006.01) | |
| *G16H 50/50* | (2018.01) | |
| *A61C 13/00* | (2006.01) | |
| *A61B 1/00* | (2006.01) | |
| *A61B 1/32* | (2006.01) | |
| *A61C 19/06* | (2006.01) | |
| *A61C 19/10* | (2006.01) | |
| *A61C 7/12* | (2006.01) | |
| *A61C 19/04* | (2006.01) | |

(52) U.S. Cl.
CPC ...... *A61C 13/0004* (2013.01); *G06K 9/00214* (2013.01); *G06T 7/33* (2017.01); *G06T 7/73* (2017.01); *G06T 17/00* (2013.01); *G16H 50/50* (2018.01); *A61B 1/00009* (2013.01); *A61B 1/32* (2013.01); *A61B 5/742* (2013.01); *A61B 2576/02* (2013.01); *A61C 7/12* (2013.01); *A61C 19/04* (2013.01); *A61C 19/066* (2013.01); *A61C 19/10* (2013.01); *A61C 2007/004* (2013.01); *G06K 2209/05* (2013.01); *G06T 2207/30004* (2013.01); *G06T 2207/30036* (2013.01); *G06T 2210/41* (2013.01)

(58) Field of Classification Search
CPC ..... A61C 2007/004; A61C 7/12; A61C 19/04; G06K 9/00214; G06K 2209/05; G06T 17/00; G06T 7/33; G06T 7/73; G06T 2207/30036; G06T 2210/41; G16H 50/50
See application file for complete search history.

(56) References Cited

U.S. PATENT DOCUMENTS

| | | |
|---|---|---|
| 6,431,870 B1 | 8/2002 | Sachdeva |
| 6,793,489 B2 | 9/2004 | Morris et al. |
| 8,562,338 B2 | 10/2013 | Kitching et al. |
| 8,684,729 B2 | 4/2014 | Wen |
| 9,572,637 B2 | 2/2017 | Jinkyun |
| 9,861,451 B1 | 1/2018 | Davis |
| 2002/0015934 A1 | 2/2002 | Rubbert et al. |
| 2003/0224314 A1 | 12/2003 | Bergersen |
| 2004/0038168 A1 | 2/2004 | Choi et al. |
| 2004/0252303 A1 | 12/2004 | Giorgianni et al. |
| 2005/0048432 A1 | 3/2005 | Choi et al. |
| 2005/0123180 A1 | 6/2005 | Luo et al. |
| 2006/0127854 A1 | 6/2006 | Wen |
| 2006/0136267 A1 | 6/2006 | Brackett et al. |
| 2006/0177789 A1 | 8/2006 | O'Bryan |
| 2006/0199140 A1 | 9/2006 | Wen |
| 2006/0199142 A1 | 9/2006 | Liu et al. |
| 2008/0306724 A1 | 12/2008 | Kitching et al. |
| 2009/0291417 A1 | 11/2009 | Rubbert et al. |
| 2010/0042440 A1 | 2/2010 | Joao |
| 2011/0268327 A1 | 11/2011 | Getto et al. |
| 2013/0017506 A1 | 1/2013 | Parker |
| 2013/0044932 A1 | 2/2013 | Caligor et al. |
| 2013/0059262 A1 | 3/2013 | Farrell |
| 2013/0215383 A1 | 8/2013 | Siminou |
| 2013/0286174 A1 | 10/2013 | Urakabe |
| 2013/0345524 A1 | 12/2013 | Meyer et al. |
| 2014/0204118 A1 | 7/2014 | Berry et al. |
| 2014/0221819 A1* | 8/2014 | Sarment ................ A61B 5/064 600/424 |
| 2014/0379356 A1 | 12/2014 | Sachdeva et al. |
| 2015/0157209 A1 | 6/2015 | Dantus |
| 2016/0012182 A1 | 1/2016 | Golay |
| 2016/0228212 A1 | 8/2016 | Salah et al. |
| 2017/0215998 A1 | 8/2017 | Kopelman et al. |

FOREIGN PATENT DOCUMENTS

| | | |
|---|---|---|
| WO | 2001/051005 A2 | 7/2001 |
| WO | 2006/065955 A2 | 6/2006 |
| WO | 2013/090843 A1 | 6/2013 |
| WO | 2015-082300 A1 | 6/2015 |

OTHER PUBLICATIONS

Dec. 8, 2014 Written Opinion issued in International Patent Application No. PCT/IB2014/064658.
Apr. 7, 2017 Office Action Issued in U.S. Appl. No. 15/023,537.
Braces Guide: Retainer Check Appointments (2015).
Fleischmann, Georg, "Cenon: The CAM User's Guide, Version 4.0", http://www.Cenon.com, pp. 1-174 (2014).
Toet, Alexander, "Target Detection and Recognition through Contour Matching", CALMA Report CALMA.TNO.WP31.AT.95b, pp. 1-32 (1994).
"Smile Capture", Style Italiano, www.styleitaliano.org/smile-capture/, pp. 1-20, 2014 (retrieved Aug. 8, 2015).
Ahmad, Irfan, "Digital dental photography Part 8: intra-oral set-ups", British Dental Journal, vol. 207, pp. 151-157 (2009).
U.S. Appl. No. 15/023,537, filed Mar. 21, 2016 in the name of Salah et al.
Jan. 7, 2016 Written Opinion issued in International Patent Application No. PCT/EP2015/074895.
U.S. Appl. No. 15/522,523, filed Apr. 27, 2017 in the name of Salah et al.
Jan. 12, 2016 Written Opinion issued in International Patent Application No. PCT/EP2015/074896.
U.S. Appl. No. 15/522,520, filed Apr. 27, 2017 in the name of Salah et al.
Feb. 24, 2016 Written Opinion issued in International Patent Application No. PCT/EP2015/074868.
U.S. Appl. No. 15/522,576, filed Apr. 27, 2017 in the name of Salah et al.
Jan. 26, 2016 Written Opinion issued in International Patent Application No. PCT/EP2015/074897.
U.S. Appl. No. 15/522,554, filed Apr. 27, 2017 in the name of Salah et al.
Jan. 13, 2016 Written Opinion issued in International Patent Application No. PCT/EP2015/074900.
U.S. Appl. No. 15/522,430, filed Apr. 27, 2017 in the name of Salah et al.
Feb. 18, 2016 Written Opinion issued in International Patent Application No. PCT/EP2015/074859.
Nov. 21, 2017 Office Action issued in U.S. Appl. No. 15/023,537.
Krieger, "It's not about the dental camera . . . ," Blog. Dental Photography Pearls for Better Images Instantly. Blogspot, Mar. 14, 2012, Published. Web., Nov. 9, 2017 Accessed. <http://dentalphotography.blogspot.com/2012/03/its-not-aboutcamera_14.html#WgTKKzN950R>.
Jul. 3, 2018 Office Action issued in U.S. Appl. No. 15/522,576.
Nov. 29, 2018 Office Action issued in U.S. Appl. No. 15/522,554.
Dec. 18, 2018 Office Action issued in U.S. Appl. No. 15/023,537.
Jan. 2, 2019 Office Action issued in U.S. Appl. No. 15/522,520.
Jan. 4, 2019 Office Action issued in U.S. Appl. No. 15/522,576.
Jul. 27, 2020 Office Action issued in U.S. Appl. No. 15/522,523.

* cited by examiner

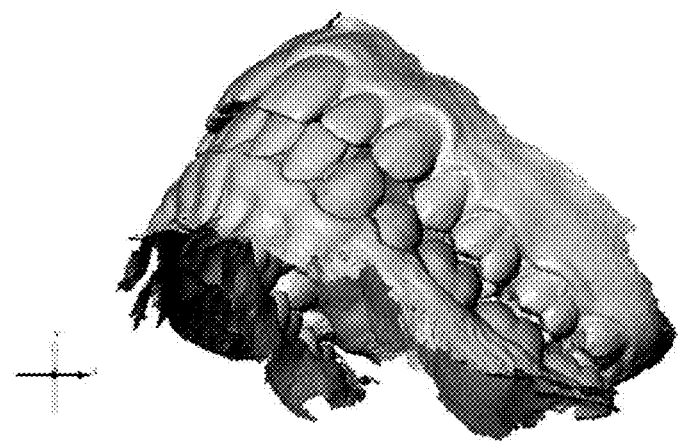
Fig.2
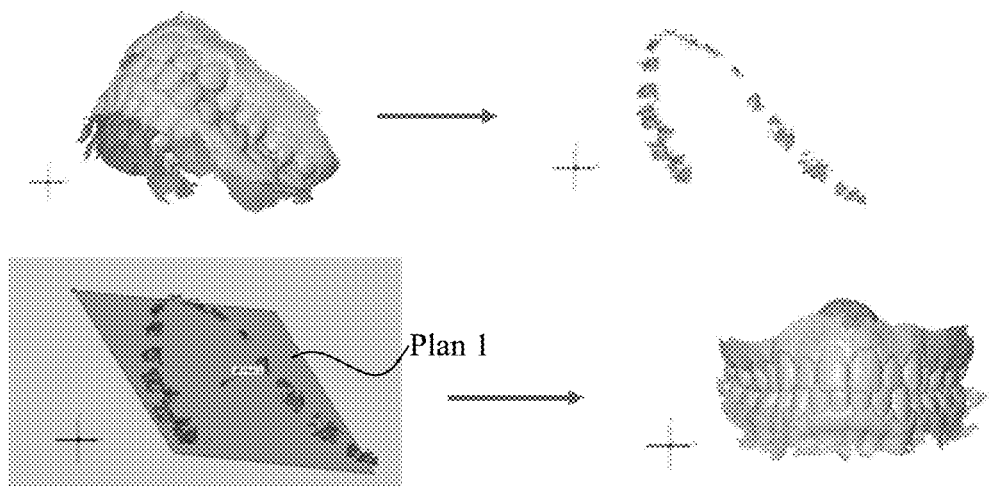
Fig.3
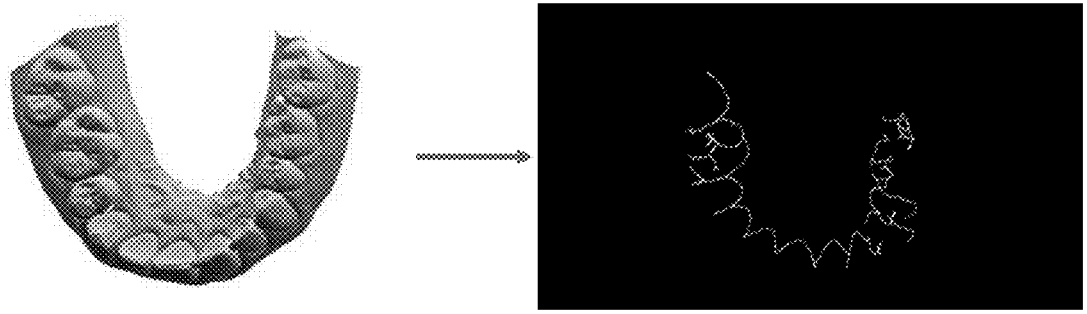
Fig. 4a                              Fig. 4b

US 10,779,909 B2

METHOD FOR MONITORING AN ORTHODONTIC TREATMENT

This is a Continuation-in-Part of Application Ser. No. 15/522,606 filed Apr. 27, 2017, which in turn is a National Stage Entry of International Application No. PCT/EP2015/074859 filed Oct. 27, 2015, which claims the benefit of French Application No. 14 60310 filed Oct. 27, 2014. The disclosure of the prior applications is hereby incorporated by reference herein in its entirety.

TECHNICAL FIELD

The present invention relates to a method for monitoring the positioning of teeth of a patient and a computer program for implementing this method.

STATE OF THE ART

It is desirable for each person to have his or her dentition checked regularly, particularly in order to check that the position of his or her teeth is not changing for the worse. During orthodontic treatment, this change for the worse may notably lead to a change of treatment. After an orthodontic treatment, this change for the worse, called "recurrence", may lead to a resumption of a treatment. Finally, more generally and independently of any treatment, each person may want to track any movement of his or her teeth.

Conventionally, the checks are performed by an orthodontist or a dentist who alone have appropriate apparatus. These checks are therefore costly. Furthermore, the visits are restrictive.

US 2009/0291417 describes a method making it possible to create, then modify, three-dimensional models, notably for the production of orthodontic appliances.

One aim of the present invention is to address, at least partially, the abovementioned problems.

SUMMARY OF THE INVENTION

The invention provides a method for monitoring the positioning of the teeth of a patient, said method comprising the following steps:
  a) production of a three-dimensional digital reference model of the arches of the patient, or "initial reference model" and, for each tooth, definition, from the initial reference model, of a three-dimensional digital reference model of said tooth, or "tooth model";
  b) acquisition of at least one two-dimensional image of said arches, called "updated image", in actual acquisition conditions;
  c) analysis of each updated image and production, for each updated image, of an updated map relating to a discriminating piece of information;
  d) optionally, determination, for each updated image, of rough virtual acquisition conditions approximating said actual acquisition conditions;
  e) searching, for each updated image, for a final reference model corresponding to the positioning of the teeth during the acquisition of the updated image, the search being preferably performed by means of a metaheuristic method, preferably evolutionist, preferably by simulated annealing, and
  f) for each tooth model, comparison of the positionings of said tooth model in the initial reference model and in the reference model obtained at the end of the preceding steps, called "final reference model", in order to determine the movement of the teeth between the steps a) and b).

As will be seen in more detail hereinbelow in the description, a method according to the invention makes it possible, from a simple image of the teeth, taken without precise prepositioning of the teeth relative to the image acquisition apparatus, for example from a photograph taken by the patient, to assess accurately the movement of the teeth from the production of the initial reference model. This assessment may also be performed by a simple computer or a mobile phone.

Preferably, the step e) comprises:
  a first optimization operation making it possible to search for the virtual acquisition conditions best corresponding to the actual acquisition conditions in a reference model to be tested determined from the initial reference model, and
  a second optimization operation making it possible to search for, by testing a plurality of said reference models to be tested, the reference model best corresponding to the positioning of the teeth of the patient during the acquisition of the updated image in the step b).

Preferably, a first optimization operation is performed for each test of a reference model to be tested during the second optimization operation.

Preferably, the first optimization operation and/or the second optimization operation, preferably the first optimization operation and the second optimization operation, implement a metaheuristic method, preferably evolutionist, preferably a simulated annealing.

Preferably, the step e) comprises the following steps:
  e1) definition of the reference model to be tested as being the initial reference model then,
  e2) according to the following steps, testing of the virtual acquisition conditions with the reference model to be tested in order to finely approximate said actual acquisition conditions;
    e21) determination of virtual acquisition conditions to be tested;
    e22) production of a two-dimensional reference image of the reference model to be tested in said virtual acquisition conditions to be tested;
    e23) processing of the reference image to produce at least one reference map representing said discriminating piece of information;
    e24) comparison of the updated and reference maps so as to determine a value for a first assessment function, said value for the first assessment function depending on the differences between said updated and reference maps and corresponding to a decision to continue or to stop the search for virtual acquisition conditions approximating said actual acquisition conditions with greater accuracy than said virtual acquisition conditions to be tested determined on the last occurrence of the step e21);
    e25) if said value for the first assessment function corresponds to a decision to continue said search, modification of the virtual acquisition conditions to be tested, then return to the step e22);
  e3) determination of a value for a second assessment function, said value for the second assessment function depending on the differences between the updated and reference maps in the virtual acquisition conditions best approximating said actual acquisition conditions and resulting from the last occurrence of the step e2), said value for the second assessment function corresponding to a decision to continue or to stop the search for a reference model approximating the positioning of the teeth during the acquisition of the updated image with greater accuracy than said reference model to be tested used on the last occurrence of the step e2), and if said value for the second assessment function corresponds to a decision to continue said search, modification of the reference model to be tested by movement of one or more tooth models, then return to the step e2).

A method according to the invention may also comprise one or more of the following optional features:

in the step a), an occlusal plane is determined according to the following operations:
  I. determination of the points of the initial reference model which belong to an arch and which are at a distance from the other arch which is less than a predetermined distance, preferably at a distance less than 3 mm from the other arch, called "points of contact";
  II. optionally, filtering of some of the points of contact, preferably such that the number of points of contact belonging to the upper arch is identical to the number of points of contact belonging to the lower arch, preferably by eliminating the points of an arch that are furthest away from the other arch;
  III. linear regression, preferably by the least squares method, over all the points of contact remaining so as to determine the occlusal plane;

in the step a), the following operations are performed:
  i. projection, in an occlusal plane, of the points of contact between the teeth of the upper and lower arches of the patient, the points of contact and/or the occlusal plane being preferably determined, according to steps I to III;
  ii. determination of the barycenter of the projections of said points of contact and creation of a reference frame, in the occlusal plane, centered on said barycenter;
  iii. determination, in said reference frame, of the parabolic function exhibiting the greatest coefficient of correlation with all the projections of the points of contact;
  iv. rotation of all the projections of the points of contact about the barycenter, and repeating of the preceding operation iii until all the projections of the points of contact have covered a determined sector, preferably greater than 90°, greater than 180°, even approximately 360°;
  v. identification of the highest coefficient of correlation for all the angular positions of all the projections of the points of contact about the barycenter, and of the axis of the corresponding parabolic function;
  vi. determination of a median longitudinal plane of the initial reference model, said plane passing through said axis and being at right angles to the occlusal plane;

in the step a), a tooth model is at least partially delimited according to the following operations:
  i'. determination, at least partially, of interior and exterior gingival edges of the arch of the tooth concerned, preferably by analysis of the variations of the orientation of the surface of the initial reference model;
  ii'. projection, in the occlusal plane, of the interior and exterior gingival edges;
  iii'. identification of the deformations of the projections of the interior and exterior gingival edges corresponding to interdental regions, the tops of these deformations being called "point of convergence" (in an interdental region, the two projections each have a point, the two points pointing substantially toward one another, the end of one point being a point of convergence);
  iv'. determination of the shortest path, on the surface of the initial reference model, between two points of convergence of interior and exterior gingival edges, respectively, of an interdental region, preferably by a metaheuristic method, preferably evolutionist, preferably by simulated annealing, said shortest path at least partially delimiting a tooth model;

an updated image is acquired less than seven days after the step a), then the steps c) to f) are implemented from this updated image;

in the step b), a hand-held acquisition apparatus is used (and in particular one which is not immobilized, for example by means of a support resting on the ground) and/or the head of the patient is not immobilized;

in the step b), an individual apparatus is used that is chosen from the group formed by a connected camera, a smart watch, a digital tablet, a portable 3D scanner and a computer coupled to an image acquisition system, such as a webcam or a digital camera, to implement the step b) and, preferably at least one of the steps, preferably all of the steps c) to f);

in the step b), an image acquisition apparatus is used that provides an updated infrared image;

in the step b), a separator is used comprising one, preferably more than two register marks, preferably non-aligned, and, preferably, the representation of the register marks on the updated image is used to
  in the step c), recut the image and/or,
  in the step d), roughly assess the actual acquisition conditions;

in the step c), the discriminating piece of information is chosen form the group consisting of a piece of outline information, a piece of color information, a piece of density information, a piece of distance information, a piece of brightness information, a piece of saturation information, an information on glare and combinations of the above pieces of information;

in the step d), data supplied by the acquisition apparatus and, preferably, concerning its orientation, are used;

in the step e2), the virtual acquisition conditions sought comprise calibration parameters of the acquisition apparatus implemented in the step b);

an optimization is implemented by a metaheuristic method, preferably evolutionist, preferably by simulated annealing to:
  in the step a), at least partially determine a gingival edge delimiting a tooth model and/or,
  in the step e2), search for the virtual acquisition conditions corresponding to the actual acquisition conditions and/or,
  in the step e), search for a reference model corresponding to the updated image;

said metaheuristic method is chosen from the group formed by
  the evolutionist algorithms, preferably chosen from: evolution strategies, genetic algorithms, differential evolution algorithms, distribution estimation algorithms, artificial immunity systems, Shuffled Complex Evolution path recomposition, simulated annealing, ant colony algorithms, particle swarm optimization algorithms, taboo search, and the GRASP method;

the kangaroo algorithm, the Fletcher and Powell method, the noise method, stochastic tunneling, hill climbing with random restarts, the cross entropy method, and hybrids of the metaheuristic methods described above.

Preferably, the step b) is executed by a person without any university training in orthodontics and/or outside of any medical, dentistry or orthodontics practice, and/or without recourse to a device for mechanically stabilizing the acquisition apparatus and/or without recourse to appliances other than a mobile phone and/or without recourse to a standard calibration gauge.

The invention also relates to the use of a method according to the invention for detecting a recurrence, and/or determining a rate of evolution of a change of positioning of the teeth, and/or optimizing the date on which an appointment is made with an orthodontist or a dentist, and/or assessing the effectiveness of an orthodontic treatment, and/or assessing the evolution of the positioning of teeth toward a theoretical model corresponding to a determined positioning of the teeth, in particular an enhanced positioning of the teeth, and/or dentistry.

The method may notably be implemented during an orthodontic treatment, notably to monitor the progress thereof, the step a) being implemented less than three months, less than two months, less one month, less than one week, less than two days after the start of the treatment, that is to say after the fitting of an appliance intended to correct the positioning of the teeth of the patient, called "active retaining appliance".

The method may also be implemented after an orthodontic treatment, to check that the positioning of the teeth does not evolve unfavorably ("recurrence"). The step a) is then preferably implemented less than three months, less than two months, less than one month, less than one week, less than two days after the end of the treatment, that is to say after the fitting of an appliance intended to hold the teeth in position, called "passive retaining appliance".

The invention also relates to:

a computer program, and in particular an application specifically for mobile phones, comprising program code instructions for the execution of one or more, preferably all, of the steps b) to f), when said program is run by a computer, a computer medium on which is stored such a program, for example a memory or a CD-ROM, and a personal appliance, in particular a mobile phone or a tablet, in which such a program is loaded.

The invention finally relates to a system comprising a three-dimensional scanner capable of implementing the step a) of a method according to the invention, a personal appliance, preferably a mobile phone, loaded with a program according to the invention.

Definitions

A "patient" should be understood to mean any person for whom a method is implemented in order to monitor the teeth thereof, whether this person is sick or not.

A "dental health professional" should be understood to mean a dentist, an orthodontist or an orthodontic laboratory.

A "dentist" should be understood to be a dentist or a dental assistant working under the responsibility of a dentist.

"Dentition" should be understood to mean the two dental arches of the patient.

A "mobile phone" is an appliance weighing less than 500 g, provided with a sensor enabling it to capture images, capable of exchanging data with another appliance more than 500 km away from the mobile phone, and capable of displaying said data, and notably said images.

The "acquisition conditions" specify the position and the orientation in space of an image acquisition apparatus in relation to the teeth of the patient or to a tooth model of the patient, and preferably the calibration of this image acquisition apparatus.

The "calibration" of an acquisition apparatus is made up of all the values of the calibration parameters. A calibration parameter is a parameter intrinsic to the acquisition apparatus (unlike its position and its orientation), the value of which influences the image acquired. For example, the diaphragm aperture is a calibration parameter which modifies the depth of field. The exposure time is a calibration parameter which modifies the brightness (or "exposure") of the image. The focal distance is a calibration parameter which modifies the viewing angle, that is to say the degree of "zoom". The "sensitivity" is a calibration parameter which modifies the response of the sensor of a digital acquisition apparatus to the incident light.

Preferably, the calibration parameters are chosen from the group formed by the diaphragm aperture, the exposure time, the focal distance and the sensitivity.

The "occlusal plane" is the plane which provides the best linear correlation with all the points of contact between the teeth of the upper arch on the one hand and the teeth of the lower arch on the other hand.

The "median longitudinal plane" is the plane substantially vertical when the patient holds the head straight, which substantially symmetrically separates left and right parts of each arch.

A "tablet" is a portable computer with touchscreen.

A 3D scanner is an apparatus making it possible to obtain a three-dimensional representation of an object.

An "image" is understood to be a two-dimensional image, like a photograph. An image is formed by pixels.

A "discriminating piece of information" is a characteristic information which may be extracted from an image ("image feature"), conventionally by a computer processing of this image.

A discriminating piece of information may have a variable number of values. For example, an outline information may be equal to one or zero depending on whether a pixel belongs or does not belong to an outline. A brightness information may take a large number of values. The processing of the image makes it possible to extract and quantify the discriminating information.

Acquisition conditions are called "virtual" when they correspond to a simulation in which the acquisition apparatus would be in said acquisition conditions (theoretical positioning and preferably calibration of the acquisition apparatus).

"Comprising a" or "including a" or "having a", should be understood to mean "including at least one", unless indicated otherwise.

BRIEF DESCRIPTION OF THE FIGURES

Other features and advantages of the invention will become more apparent on reading the following detailed description and on studying the attached drawing in which:

FIG. 2 represents an example of an initial reference model, FIG. 3 illustrates the processing performed to determine the occlusal plane, FIG. 4 (4a-4d) illustrates the step necessary for determining the tooth models in a reference model, FIG. 5 (5a-5d) illustrates the acquisition of updated images, and the trimming operation, FIG. 6 (6a-6b) illustrates the processing of an updated image making it possible to determine the outline of the teeth, and FIG. 7 schematically illustrates the relative position of register marks 12 on updated images $14_1$ and $14_2$ of a separator 10, depending on the direction of observation (broken line)

DETAILED DESCRIPTION

Figure 1:
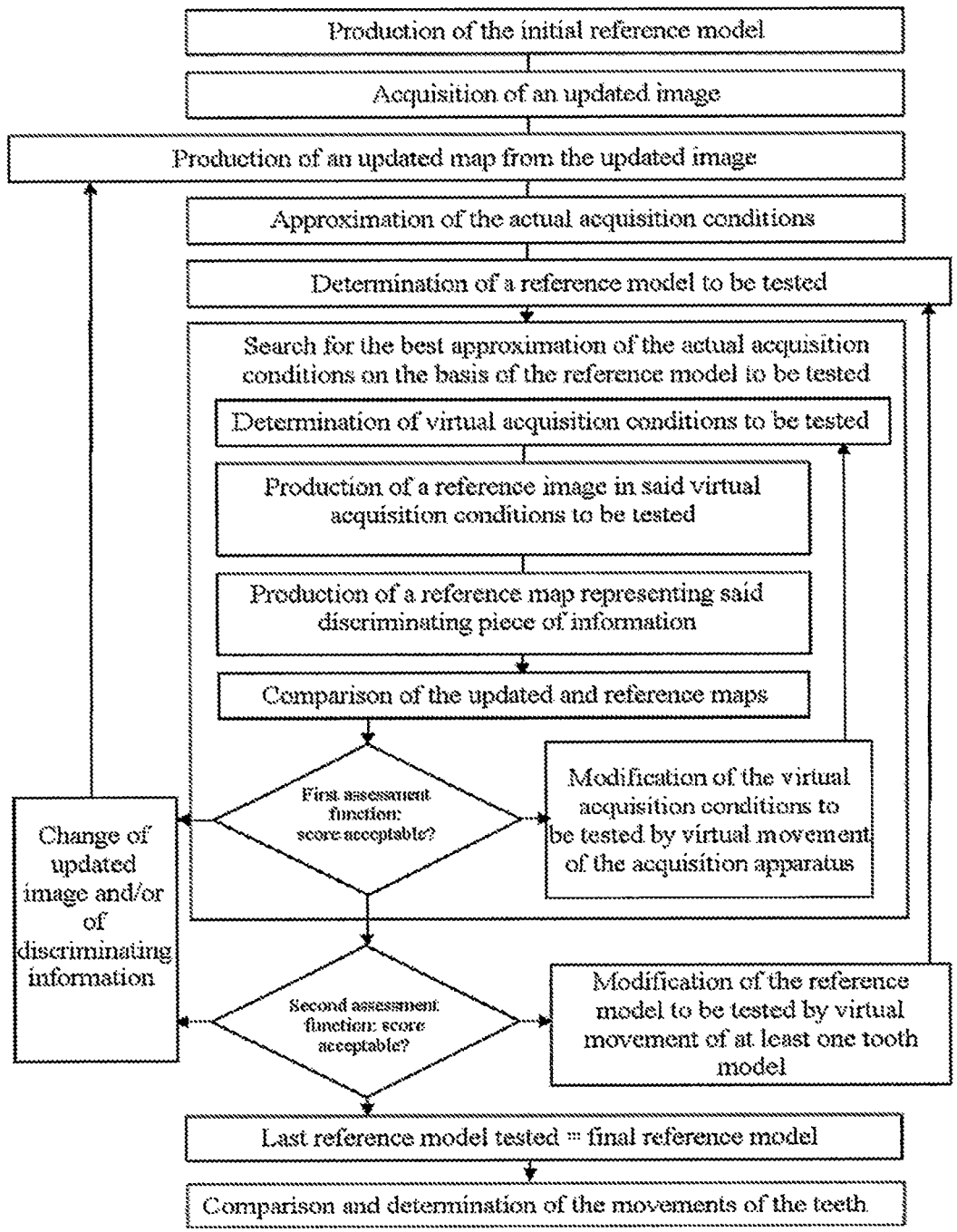
FIG. 1 represents a flow diagram illustrating the implementation of a method according to the invention.

A method according to the invention comprises the steps mentioned above.

In the step a), an initial reference model of the arches, or of a part of the arches of the patient is created (see FIG. 2).

The initial reference model is a digital model in three dimensions of the arches of the patient, for example of .stl or .Obj, .DXF 3D, IGES, STEP, VDA, or point cloud type. Advantageously, such a model, called "3D" may be observed from any angle.

For the tracking of an orthodontic treatment, the initial reference model is preferably prepared at the start of the treatment. The initial reference model may correspond to a positioning of the teeth of the patient before the treatment or to a positioning of the teeth of the patient that the treatment sets out to achieve. In this case, the initial reference model is conventionally computed from a first three-dimensional model corresponding to the positioning of the teeth of the patient before the treatment.

To monitor for recurrence, the initial reference model is preferably prepared less than six months, preferably less than three months, even more preferably less than a month after the end of the orthodontic treatment, generally immediately after the end of the treatment. It thus corresponds to a substantially optimum positioning of the teeth.

The initial reference model may also be prepared independently of any treatment, for example because the patient wants to monitor the movements of his or her teeth.

The initial reference model may be prepared from measurements performed on the teeth of the patient or on a physical model of his or her teeth, for example a plaster model.

The initial reference model is preferably created by means of a professional apparatus, for example by means of a 3D scanner, preferably implemented by a health professional, for example by an orthodontist or an orthodontic laboratory. In an orthodontic practice, the patient or the physical model of his or her teeth may advantageously be arranged in a precise position and the professional apparatus may be refined. The result thereof is a very accurate initial reference model. The initial reference model preferably provides an information on the positioning of the teeth with an error of less than 5/10 mm, preferably less than 3/10 mm, preferably less than 1/10 mm.

Orientation of the initial reference model:

Preferably, the orientation of the initial reference model in space, and in particular, preferably, the occlusal plane and the median longitudinal plane, are determined.

The occlusal plane and the median longitudinal plane may be determined manually, approximately. The inventors have however discovered methods that make it possible to determine these planes by computer processing.

Preferably, the reference model is a model of the arches with mouth closed, that is to say in a position in which teeth of the upper arch are in contact with teeth of the lower arch.

Conventionally, the initial reference model supplied by a three-dimensional scanner makes it possible to distinguish the upper arch from the lower arch. Generally, the model is supplied in the form of two files corresponding respectively to these arches, and comprising data making it possible to position the models of these arches relative to one another in the occlusal position.

Preferably, to estimate the points of contact between the teeth of the upper and lower arches, the set of the points of the model of the upper arch and of the lower arch which are at a distance less than a predetermined limit is determined, this limit preferably being less than 3 mm, preferably approximately 2 mm. All the other points of these models are then disregarded, which results in the representation of FIG. 3b. A linear regression then makes it possible to determine the occlusal plane ("plane 1" in FIG. 3c).

The initial reference model may thus be oriented according to the occlusal plane (FIG. 3d).

If the initial reference model does not comprise data making it possible to position the upper and lower arches relative to one another, a check-bite is preferably used, revealing the points of contact between the upper teeth and the lower teeth, then the models of the upper and lower arches are repositioned in relation to this check-bite.

The median longitudinal plane is at right angles to the occlusal plane, but its orientation is unknown.

Preferably, the following procedure is applied to determine the orientation of the median longitudinal plane:

Axes [Ox) and [Oy) are considered in the occlusal plane, the point O being the barycenter of the normal projections of the points of contact on the occlusal plane.

In this reference frame (xOy), the curve, preferably parabolic, is sought which exhibits the greatest coefficient of correlation with the set of said projections.

The set of the projections of the points of contact is then moved in the occlusal plane, by rotation about the point O, and the preceding step is recommenced from this new angular position of the projections of the points of contact.

The cycle of the above operations is continued, preferably until the set of the points of contact has been rotated by 360° about the barycenter O. The coefficients of correlation corresponding to the different orientations of the set of the points of contact are then compared. The axis of the curve which leads to the highest coefficient of correlation is then considered as included in the median longitudinal plane, which makes it possible to precisely define the orientation thereof.

The orientation in space of the initial reference model is thus perfectly determined, rapidly.

Creation of the Tooth Models

In the initial reference model, a part which corresponds to a tooth, or "tooth model", is delimited by a gingival edge which may be broken down into an interior gingival edge (on the side of the interior of the mouth relative to the tooth), an exterior gingival edge (oriented toward the exterior of the mouth relative to the tooth) and two lateral gingival edges. The gingival edges correspond to regions in which the orientation of the surface defined by the initial reference model undergoes modifications of high amplitudes. These variations of orientation may be identified according to known techniques, for example by identifying the changes of direction of the normal to the surface modelled. FIG. 4*a* represents a view of the initial reference model processed to show these changes of direction. FIG. 4*b* shows the interior gingival edge which may be extracted by analysis of the image of FIG. 4*a*.

Figure 4C:

Several views of the initial reference model are thus analyzed, which makes it possible to determine the interior and exterior gingival edges in three dimensions, as represented in FIG. 4*c*.

Moreover, in projection in the occlusal plane, the interior and exterior gingival outlines of an arch approach one another on either side of a tooth. To determine a lateral gingival edge of a tooth, the shortest path is sought, on the surface of the initial reference model, between the two points of the interior and exterior gingival edges thus brought closer together and which substantially face one another. The search for the shortest path between two points on a three-dimensional model involves optimization techniques that are well known. Preferably, this search results from a metaheuristic method, preferably evolutionist, preferably from a simulated annealing.

Figure 4D:
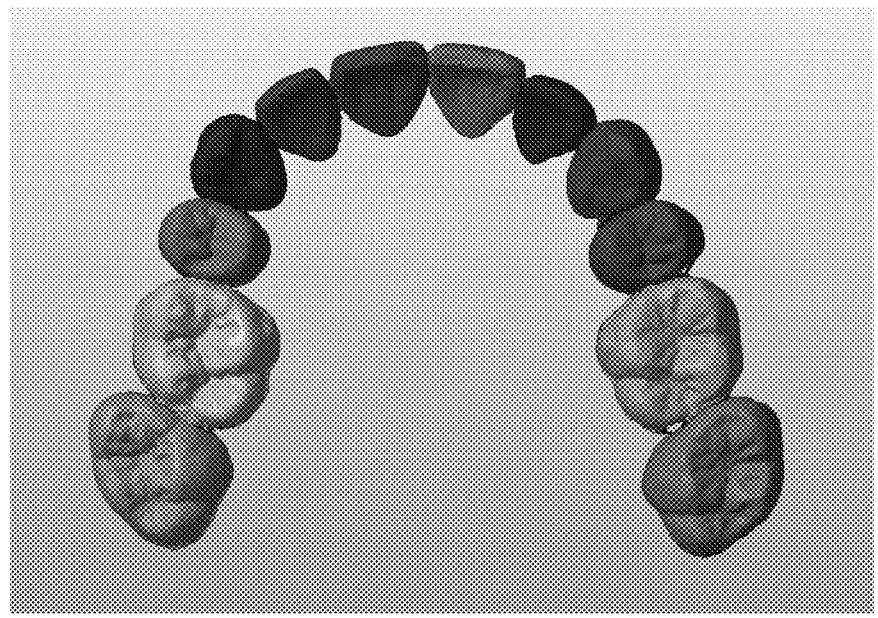

Two adjacent lateral gingival edges and the parts of the interior and exterior gingival edges which connect these lateral gingival edges thus make it possible to delimit a tooth at the gingival level. By taking account of the fact that a tooth extends from the gingival outline to the occlusal plane, it is thus possible to determine the parts of the initial reference model which correspond to the different teeth ("tooth models"). FIG. 4*d* represents the set of the tooth models of an arch.

The initial reference model may be stored in a centralized database, comprising the initial reference models of a plurality of patients. This database may be physically installed in a specialist establishment. It may also be installed in a laboratory or an orthodontic practice, which limits the transfers of confidential information.

In one embodiment, the initial reference model is handed to the patient. Preferably, a computer file corresponding to the initial reference model is stored on a removable medium, for example on a USB key or on an electronic card, preferably on a mobile phone, a tablet or a portable computer of the patient, and in particular on the personal appliance which will preferably be used in the steps b) and subsequent steps. Preferably, the patient or a dental health professional loads the initial reference model in said individual appliance or makes it available for loading in said individual appliance. The patient preferably loads the initial reference model from the Internet.

In a preferred embodiment, the reference model is not handed to the patient. Preferably, the reference model is only made available to a specialist establishment for implementing the steps c) to f). It may remain stored in the establishment in which it was produced in the step a) and where, preferably, the steps c) to f) are implemented.

In the step b), an updated image is taken of the arches by means of an image acquisition apparatus. The step b) is preferably performed by the patient or one of his or her close relatives, but may be performed by a dentist.

Moment of Acquisition

Preferably, the updated image is taken after a time interval $\Delta t$ after the step a). The time interval $\Delta t$ may be predetermined. It may be constant, regardless of the occurrence of the method, that is to say that this interval relates to the first execution of the method or a subsequent execution. It may be variable, and depend for example on the results obtained following an earlier execution of the method. In particular, to monitor recurrence, the time interval $\Delta t$ may be even shorter when this execution has made it possible to detect a significant drift.

In a preferred embodiment, the time interval $\Delta t$ is determined by the orthodontist, according to a monitoring schedule. Based on the evolution of the position of the teeth, the orthodontist may modify this schedule and accordingly modify the time interval $\Delta t$. In one embodiment, the method according to the invention is executed several times, the time intervals between each execution being able to be identical or different. The time intervals between two successive executions may all be determined before the first execution to correspond to a monitoring schedule drawn up by the orthodontist.

The time interval $\Delta t$ may also be indeterminate and depend for example on decisions of the patient. For example, the creation of an updated image may be performed on the occasion of an appointment with the dentist or at any moment when the patient so wishes, even independently of any orthodontic treatment.

The time interval $\Delta t$ is preferably determined to correspond to a potentially significant evolution of the positioning of the teeth.

For example, to monitor recurrence, the time interval $\Delta t$ is preferably less than three months in the first year after the treatment. After this first year, the time interval $\Delta t$ is preferably greater than one month, even greater than six months or greater than twelve months. In particular, to detect a drift in the teeth, a time interval of between six months and eighteen months is suitable.

Preferably, at least one reminder informing the patient of the need to create an updated image is addressed to the patient. This reminder may be in paper form or, preferably, in electronic form, for example in the form of an email, an automatic alert from the specialist mobile application or an SMS. Such a reminder may be sent by the practice or the orthodontic laboratory or by the dentist or by the specialist mobile application of the patient, for example.

In a preferred embodiment, an updated image is acquired before the teeth have been able to move significantly, substantially at the same time as the creation of the initial reference model, preferably less than 7 days, less than 3 days, less than one day after the step a), that is to say before the teeth have been able to move significantly. The implementation of the method with this updated image advantageously makes it possible to check that the method does not lead to the detection of any difference between the initial and final reference models, and therefore that it is working correctly.

In one embodiment, the updated image may be acquired before the creation of the initial reference model. For example, the steps a) and b) may be performed at the end and at the start of an orthodontic treatment, respectively. It is thus notably possible to assess the effectiveness of the treatment in the absence of a 3D model at the start of treatment. The time interval $\Delta t'$ separating the steps a) and b) in this embodiment may notably take the values described above for $\Delta t$.

Image Acquisition Apparatus

Preferably, the image acquisition apparatus is a personal appliance commonly available in the market, for example a mobile phone, a so-called "connected" camera, a so-called "smart" watch, or a tablet or a personal computer, fixed or portable, comprising an image acquisition system, like a webcam or a camera, preferably a digital camera. Even though the updated image may in particular be created by a dentist, it is preferably created by the patient him or herself or by one of his or her near relatives.

In particular, the updated image may be created by a person who has no particular knowledge of orthodontics, and in particular who has no degree in orthodontics or dentistry.

Preferably, the same acquisition apparatus is used to take all the updated images.

The image acquisition apparatus preferably weighs less than 3 kg, less than 2 kg, less than 1 kg, less than 500 g, preferably less than 300 g.

The step b) may therefore advantageously be performed at a distance from the step a), that is to say in a location different from that in which the step a) is performed, in particular at more than 50 m, more than 100 m, more than 1 km from the place where the step a) is performed, in particular outside of an orthodontic practice. In one embodiment, the step b) is not performed in a dental practice, an orthodontic practice or in an orthodontic laboratory, except, possibly, in a session intended to train the patient.

Preferably, the updated image is a photograph, in particular a panoramic photograph. In one embodiment, the updated image is extracted from a film.

In a preferred embodiment, the method uses several updated images to have at least one representation of each tooth, preferably at least three updated images corresponding to a front view, a right side view and a left side view of the teeth of the patient.

Preferably, in the step b), at least one updated image is taken in mouth closed position and at least one updated image is taken in mouth open position. The mouth closed image advantageously makes it possible to identify the relative movements between the two arches. The mouth open updated image advantageously makes it possible to clearly identify the outlines of the teeth, without the teeth of the upper arch concealing the teeth of the lower arch or vice versa.

The updated images may be taken either for the upper arch, or for the lower arch, or, preferably, for the two arches.

Several similar images (representing substantially the same teeth) may also be useful in order to search for the best score. According to the acquisition conditions, a discriminating piece of information will in particular be able to lead to different results depending on the updated image used.

Figure 5A:
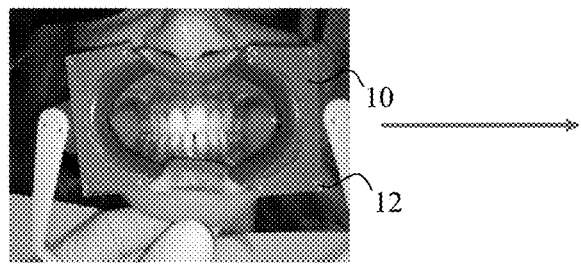
Figure 5B:
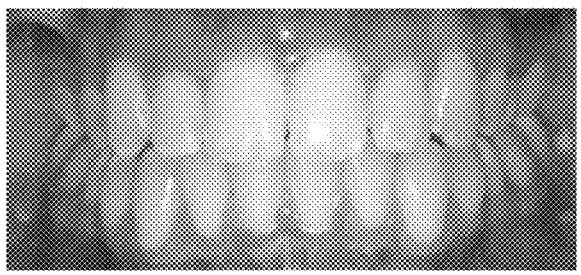
Figure 5C:
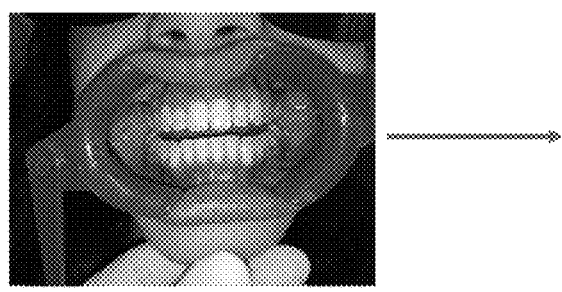
Figure 5D:
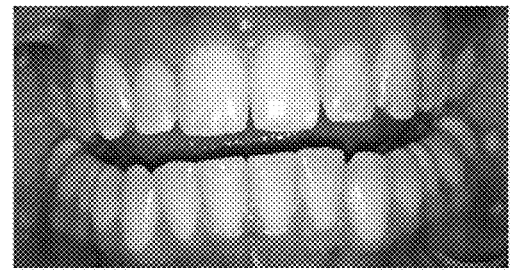

Preferably, a separator is used during the step b), as represented in FIGS. 5a and 5c. The first function of the separator is to separate the lips in order to improve the visibility of the teeth. Preferably, a separator is handed to the patient, for example at an appointment with his or her orthodontist or his or her dentist.

The image acquisition apparatus preferably supplies color images, and/or infrared images of the mouth of the patient, even of the face of the patient. The color images preferably represent the mouth of the patient with the actual colors of this mouth. The infrared images advantageously make it possible to show the teeth with an excellent contrast.

Preferably, the image acquisition apparatus comprises a specialist application making it possible to implement the step b), but also, preferably, the subsequent steps, preferably all the subsequent steps. Even more preferably, this application manages the reminders and informs the patient of the need to create an updated image.

Preferably, the specialist application is loaded into the image acquisition apparatus from a physical medium such as a USB key or a CD-ROM, or is downloaded over the Internet or wirelessly. In one embodiment, the specialist application is supplied to the patient by the practice and/or the orthodontic laboratory. It may in particular take the form of an application of the type of those commonly downloaded to iPhones of the Apple® brand or the appliances of all brands implementing the Android® operating systems or any other operating system.

The image acquisition apparatus preferably comprises a camera or a video or infrared camera, that the user, for example the patient or one of his or her close relatives, positions by means of a viewfinder or a screen, before actuating it.

Polarizing Means

A method according to the invention does not require an accurate positioning of the image acquisition apparatus relative to the teeth.

In one embodiment, no positioning constraint to ensure an arrangement of the image acquisition apparatus at less than 30 cm, less than 20 cm, less than 10 cm or less than 5 cm from a determined position is imposed.

Preferably, the image acquisition apparatus does however comprise polarizing means facilitating the approximate positioning thereof relative to the patient before the acquisition of the updated image.

The user may be guided by written and/or voice messages for the acquisition. For example, the personal appliance may announce "take a photo from the front", emit a signal to inform the user that the photo is acceptable or that, on the contrary, he or she must take another photo, announce "take a photo from the right", preferably by displaying an arrow to orient the user, etc. The end of the acquisition process may also be announced by the apparatus. The apparatus may also assist in the positioning, for example by visual messages (for example by displaying arrows), and/or audible messages (like a succession of beeps whose frequency increases as the positioning of the apparatus improves), and/or written and/or voice messages ("higher", "lower", etc.).

The polarizing means may in particular comprise references which appear on the viewfinder or the screen. The references may for example comprise a line intended to be aligned with the general direction of the join between the upper teeth and/or the lower teeth when the teeth are clamped by the patient, or a vertical line intended to be aligned with the join between the two upper incisors. The references may also refer to other parts of the patient. For example, they may consist of marks corresponding to the position of the eyes or take the form of an outline in which the mouth or the face of the patient must be positioned.

The reference or references are preferably "immobile" on the screen, that is to say that they do not move on the screen when the acquisition apparatus is moving.

In a preferred embodiment, the reference or references each correspond to a register mark borne by a reference frame added to the patient, that is to say that the patient did not have before the implementation of the method, preferably borne by a dental separator. A reference frame may also be a piece bitten on by the patient.

The register mark may have a surface area greater than 0.5 $mm^2$, preferably greater than 1 $mm^2$, preferably greater than 2 $mm^2$, preferably greater than 5 $mm^2$, preferably greater than 10 $mm^2$, even greater than 20 $mm^2$, even greater than 30 $mm^2$, and/or less than 50 $mm^2$.

Large dimensions conferred on a register mark or a proliferation of register marks advantageously make it possible to improve the accuracy of the positioning of the acquisition apparatus.

The register marks may be identical or different.

The register marks may notably be different according to their position, for example according to whether they are in the upper part or the lower part of the reference frame, and in particular of the separator, or to the right or to the left of the reference frame, and in particular the separator.

The register mark may be identical or different from the corresponding reference. It is preferably of geometrical shape, for example a dot, one or more lines, for example parallel, a star, a circle, an oval, a regular polygon, notably a square, a rectangle or a rhombus.

The register mark may also be an image, a letter, a digit or a sequence of letters and/or of digits and/or a QR Code and/or a bar code.

The register mark is preferably of a different color from the surface of the separator which surrounds it, preferably so as to offer a high contrast.

A register mark may be visible or invisible to the naked eye, provided that it appears on the screen of the acquisition apparatus.

To improve the accuracy, the register marks are preferably separated from one another so that, when they correspond to their respective references on the screen, at least first and second register marks are less than 3 cm, preferably less than 2 cm, preferably less than 1 cm, preferably less than 0.5 cm, from first and second edges, respectively, of the screen. The first and second edges are preferably opposite edges of the screen.

The register mark may have one or more dimensions and/or a shape and/or a color that is/are identical or different from those of the corresponding reference.

The "correspondence" of a reference and of a register mark is a predefined arrangement relative to one another. It indicates a particular positioning of the acquisition apparatus relative to the register mark. The correspondence depends on the nature of the reference and on the register mark. The predefined situation, which corresponds to target acquisition conditions, may notably be a superimposition total or partial, a juxtaposition, or an alignment of the reference and of the register mark.

The exact superimposition of the reference and of the register mark makes it possible not only to determine the direction toward which the lens of the acquisition apparatus must point and/or the distance between the acquisition apparatus and the separator, but also, if the reference and/or the register mark are asymmetrical, the orientation of the acquisition apparatus around this direction.

The dimensions and/or the surface areas of a register mark and of the corresponding reference and/or the distance between several register marks and between the corresponding references may be used to set the distance between the acquisition apparatus and the arches.

The reference may for example be:
- a fixed line, on which the user must for example align register marks,
- a shape, preferably asymmetrical, corresponding to the shape of a register mark to be superimposed, for example a dot that the user must for example superimpose on the register mark, or a circle in which the user must for example place the register mark,
- a colored shape corresponding to the color of a register mark to be superimposed,
- a shape complementing the shape of a register mark, preferably so that the matching of the register mark and of the reference leads to a form having a direction, like a geometrical form, a letter or a text, a drawing, or a pattern, for example.

In a preferred embodiment, the references are defined, at least partially, from information supplied by the initial reference model. For example, according to the principles of "augmented reality", the reference may be a view of the initial reference model, for example a front view or a right side or a left side view of the initial reference model, made visible, transparent, on the screen of the image acquisition apparatus during the acquisition. It is thus very easy for the patient to approximately superimpose such a view with the teeth that he or she has to photograph.

In one embodiment, the positioning of the image acquisition apparatus results simply from the matching of references appearing on the screen of said acquisition apparatus with corresponding register marks, preferably with register marks of a dental separator.

In one embodiment, the reference or references which appear on the screen are determined according to the patient and/or the therapeutic treatment. In other words, the computer program is parameterized according to the patient in order for the images acquired to correspond specifically to the needs of the patient. Advantageously, at the moment of the acquisition of the images, the acquisition apparatus is therefore positioned in a substantially optimal position with respect to the particular features of the patient and/or the therapeutic treatment applied.

As will be seen in more detail hereinbelow in the description, the register marks of the separator preferably have a number of functions. First of all, they make it possible to guide the positioning of the image acquisition apparatus at the moment of the acquisition of the images, by means of corresponding references appearing on the screen of the acquisition apparatus. They also allow, in the step c), for a recropping of the updated images. Finally, the register marks, which appear on the images, make it possible, in the step d), to roughly determine virtual acquisition conditions approximating the actual acquisition conditions, which makes it possible to speed up the computer processing.

The steps c) and subsequent steps are preferably performed either on a personal appliance of the patient, preferably with the appliance used in the step b), or with an appliance of a dental health professional, or with a dedicated third party server.

In the step c), each updated image is analyzed so as to produce, for each updated image, an updated map relating to at least one discriminating piece of information.

Recropping

The analysis of the image may comprise a recropping of the updated image in order to isolate the relevant part, in particular to eliminate, at least partially, from the updated image, the elements which have not been the subject of the initial reference model, like the nose or the eyes of the patient or the separator. This recropping or "cropping", is facilitated by the representation of register marks on the updated image.

In particular, preferably, as represented in FIGS. 5a and 5c, the separator 10 bears at least three non-aligned register marks 12. If the separator is in several parts, for example conventionally in two parts, each part preferably bears at least three non-aligned register marks.

The shape of a register mark, for example an asymmetrical shape, may be also used to register the position of the separator on the updated image.

Preferably, the register marks have shapes and/or colors facilitating the identification thereof on a updated image. For example, they may be of black color while the rest of the separator is white.

In one embodiment, the register marks have shapes and/or colors making it possible to identify them individually. For example, they may each be of different color.

The identification of the register marks on the updated image makes it possible to identify the zone of the updated image containing the elements that have been the subject of the initial reference model, that is to say the teeth and the gingiva. The updated image may then be trimmed accordingly. The comparison of FIGS. 5a and 5b, or 5c and 5d, illustrates the effect of the recropping on an updated image.

Updated Map

Figure 6A:
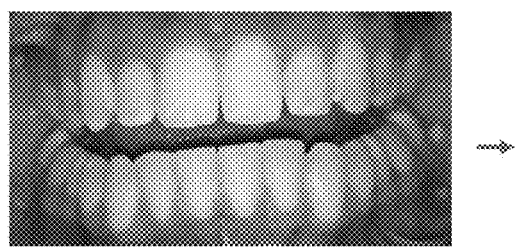
Figure 6B:

An updated map represents a discriminating piece of information in the reference frame of the updated image. For example, FIG. 6b is an updated map relating to the outline of the teeth obtained from the updated image of FIG. 6a.

The discriminating information is preferably chosen from the group consisting of a piece of outline information, a piece of color information, a piece of density information, a piece of distance information, a piece of brightness information, a piece of saturation information, a piece of information on the glare and combinations of such pieces of information.

A person skilled in the art knows how to process an updated image to show the discriminating information. This processing comprises, for example, the application of masks or filters that are well known, supplied with the image processing software.

In the optional step d), actual acquisition conditions during the step b) are roughly determined. In other words, at least the relative position of the image acquisition apparatus at the moment when the updated image was taken (position of the acquisition apparatus in space and orientation of this apparatus) is determined. The step d) advantageously makes it possible to limit the number of tests on virtual acquisition conditions during the step e), and therefore makes it possible to considerably speed up the step e).

One or more heuristic rules are preferably used. For example, preferably, there are excluded, from the virtual acquisition conditions likely to be tested in the step e), the conditions which correspond to a position of the image acquisition apparatus behind the teeth or at a distance from the teeth greater than 1 m.

Figure 7:
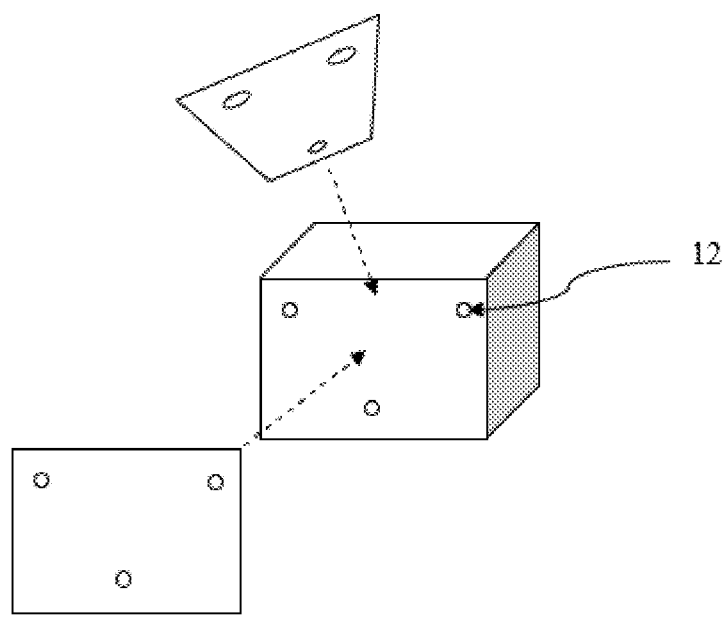

In a preferred embodiment, as illustrated in FIG. 7, register marks are used that are represented on the updated image, and in particular register marks 12 of the separator, to determine a substantially conical region of space delimiting the virtual acquisition conditions likely to be tested in the step e), or "test cone".

Specifically, there are preferably at least three non-aligned register marks 12 on the separator 10, for example, and their relative positions are measured accurately on the separator.

The register marks are then identified on the updated image, as described previously. Simple trigonometrical computations make it possible to approximately determine the direction from which the updated image has been taken. A cone oriented in this direction, the vertex of which is at the level of the separator and the half angle of which at the vertex is preferably less than 10°, preferably less than 5°, for example 3°, may then be defined as "test cone". The half-angle at the vertex corresponds to a degree of uncertainty. The smaller the half-angle at the vertex, the greater the probability that the virtual acquisition conditions corresponding to the actual acquisition conditions are outside of the test cone.

For example, when the updated image is taken at right angles to the plane of the three register marks on the separator, it may be deduced therefrom that the acquisition apparatus was substantially within a test cone whose axis is substantially at right angles to this plane during the taking of the updated image. If the relative positions of the three register marks on the updated image are different from those that the register marks occupy on the separator, the axis of the test cone within which the search for the positioning of the acquisition apparatus during the acquisition of the updated image is limited is inclined relative to the plane of the register marks, as represented in FIG. 7.

In a particular embodiment, as illustrated in FIGS. 5a and 5c, the separator comprises independent left and right parts, which each comprise at least three register marks, preferably at least four register marks. A left test cone may thus be determined by means of the register marks of the left-hand part and a right test cone may be determined by means of the register marks of the right-hand part of the separator. The virtual acquisition conditions likely to be tested may then be limited to positions of the acquisition apparatus in space belonging to these two test cones. It is also possible to consider that the best assessment of the position of the acquisition apparatus corresponds to the mean position between the best position in the left test cone and the best position in the right search cone.

The position of the register marks on the updated image also makes it possible to assess the trim of the acquisition apparatus during the capture of the updated image. For example, if it is known that two register marks are substantially aligned in a horizontal direction during the acquisition of the updated image, the direction of the straight line containing these two points on the updated image provides an indication on the orientation of the acquisition apparatus in the actual acquisition conditions.

Finally, the size of the register marks on the updated image or their spacing may make it possible to assess the distance between the image acquisition apparatus and the teeth during the acquisition of the updated image, and therefore to reduce the test cone to a truncated cone.

In the optional step d), it is also possible to use data supplied by the acquisition apparatus and concerning its orientation, for example gyroscopic data.

Preferably, in the step d), the calibration of the actual acquisition apparatus during the step b) is roughly determined.

The way in which each calibration parameter acts on the acquired image is well known. In particular, the operation of an acquisition apparatus may be conventionally modelled so as to be able to test a particular calibration on the acquired image. The inventors have inverted such a model, within no particular technical difficulty, in order, through the analysis of the representation of the separator, for it to be possible to roughly assess the calibration of the acquisition apparatus during the step b).

For example, the ratio between the surface area of the register marks on the updated image and the surface area of the updated image makes it possible to assess the focal distance of the acquisition apparatus during the step b). The representation of a register mark whose optical characteristics are known make it possible to assess the exposure time and the sensitivity.

In a preferred embodiment, a register mark is a relief which does not extend exclusively in the general plane of the separator, corresponding to a plane parallel to the frontal (or coronal) plane. Preferably, a register mark is a relief which extends in a plane substantially at right angles to the general plane of the separator. The relief may in particular take the form of a tongue which, when the separator is in its service position, extends toward the bottom of the mouth.

The analysis of the representation of this relief advantageously makes it possible to assess the depth of field. Alternatively, two register marks which are not in a same frontal plane may be used for this purpose.

The step d) allows only a rough assessment of the actual acquisition conditions. The step d) does however make it possible to determine a restricted set of virtual acquisition conditions likely to correspond to the actual acquisition conditions, and, in this set, virtual acquisition conditions constituting the best point of departure for the step e1) described hereinbelow.

The step d) also makes it possible to detect updated images unsuitable for continuing the method, for example an updated image which does not show the register marks. Preferably, the method is then restarted at the step c) with a new updated image.

Obviously, the different methods that may be implemented in the step d) may be combined.

The objective of the step e) is to modify the initial reference model to obtain a final reference model which corresponds to the updated image. Ideally, the final reference model is therefore a three-dimensional digital reference model from which the updated image could have been taken if this model had been real.

A succession of reference models "to be tested" is therefore tested, the choice of a reference model to be tested being preferably dependent on the level of match of the reference models "to be tested" previously tested with the updated image. This choice is preferably made according to a known optimization method, in particular chosen from the metaheuristic optimization methods, preferably evolutionist, in particular the simulated annealing methods.

In the step e1), it is determined that the reference model to be tested is the initial reference model during the first execution of the step e2).

In the step e2), the first step is to determine virtual acquisition conditions to be tested, that is to say a virtual position and a virtual orientation likely to match the actual position and orientation of the acquisition apparatus during the capture of the updated image, but also, preferably, a virtual calibration likely to match the actual calibration of the acquisition apparatus during the capture of the updated image.

The first virtual acquisition conditions to be tested may be random. Preferably, they are chosen from the limited set determined in the step d), and even more preferably, correspond to virtual acquisition conditions corresponding, according to the step d), to the most promising virtual acquisition conditions, that is to say those constituting the best springboard for approximating, as rapidly as possible, the actual acquisition conditions (step e21)).

The image acquisition apparatus is then virtually configured in the virtual acquisition conditions to be tested in order to acquire a reference image of the reference model in these virtual acquisition conditions to be tested. The reference image therefore corresponds to the image that the image acquisition apparatus would have taken if it had been placed, relative to the reference model to be tested, and optionally calibrated in the virtual acquisition conditions to be tested (step e22)).

If the updated image was taken at the same moment that the reference model was produced, and if the virtual acquisition conditions are exactly the actual acquisition conditions, the reference image may therefore be exactly superimposed on the updated image. The differences between the updated image and the reference image result from errors in the assessment of the virtual acquisition conditions (if they do not correspond exactly to the actual acquisition conditions) and from movements of the teeth between the step b) and the reference model to be tested.

To compare the updated and reference images, the discriminating information is compared on these two images. More specifically, from the reference image, a reference map is produced representing the discriminating information (step e23)).

The updated and reference maps, the two of them relating to the same discriminating information, are then compared and the difference between these two maps is assessed by means of a score. For example, if the discriminating information is the outline of the teeth, it is possible to compare the mean distance between the points of the outline of the teeth which appears on the reference image and the points of the corresponding outline which appears on the updated image, the score being all the higher as this distance shortens.

The score may for example be a coefficient of correlation.

Preferably, the virtual acquisition conditions comprise the calibration parameters of the acquisition apparatus. The score is all the higher as the values of the calibration parameters tested come closer to the values of the calibration parameters of the acquisition apparatus used in the step b). For example, if the diaphragm aperture tested is far from that of the acquisition apparatus used in the step b), the reference image exhibits blurred regions and sharp regions which do not correspond to the blurred regions and to the sharp regions of the updated image. If the discriminating information is the outline of the teeth, the updated and reference maps do not therefore represent the same outlines and the score will be low.

The score is then assessed by means of a first assessment function. The first assessment function makes it possible to decide whether the cycling on the step e2) must be continued or stopped. The first assessment function may for example be equal to 0 if the cycling must be stopped or be equal to 1 if the cycling must continue.

The value of the first assessment function may depend on the score reached. For example, it may be decided to continue the cycling on the step e2) if the score does not exceed a first threshold. For example, if an exact match between the updated and reference images leads to a score of 100%, the first threshold may be, for example, 95%. Obviously, the higher the first threshold, the better the accuracy of the assessment of the virtual acquisition conditions if the score comes to exceed this first threshold.

The value of the first assessment function may also depend on scores obtained with virtual acquisition conditions tested previously.

The value of the first assessment function may also depend on random parameters and/or on the number of cycles of the step e2) already performed.

In particular, it is possible, despite the repetition of the cycles, not to manage to find virtual acquisition conditions which are sufficiently close to the actual acquisition conditions for the score to reach said first threshold. The first assessment function may then lead to the decision to quit the cycling although the best score obtained has not reached said first threshold. This decision may result, for example, from a number of cycles greater than a predetermined maximum number.

A random parameter in the first assessment function may also authorize the continuation of tests of new virtual acquisition conditions, although the score appears satisfactory.

The assessment functions conventionally used in the metaheuristic, preferably evolutionist, optimization methods, particularly in the simulated annealing methods, may be used for the second assessment function.

If the value of the first assessment function indicates that it is decided to continue the cycling in the step e2), the virtual acquisition conditions tested (step e25)) are modified and a cycle (step e2)) is recommenced consisting in producing a reference image and a reference map, then in comparing this reference map with the updated map to determine a score.

The modification of the virtual acquisition conditions corresponds to a virtual movement in space and/or to a modification of the orientation and/or, preferably, to a modification of the calibration of the acquisition apparatus. This modification may be random, provided however that the new virtual acquisition conditions to be tested still belong to the set determined in the step d). The modification is preferably guided by heuristic rules, for example by favoring the modifications which, according to an analysis of the preceding scores obtained, appear the most favorable to increase the score.

Figure 8A:
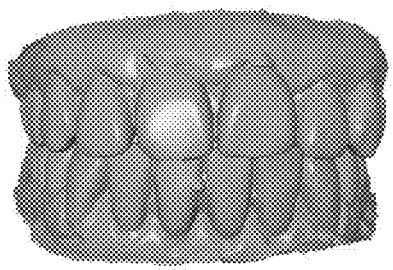
FIGS. 8a and 8b illustrate two views of a three-dimensional model with two different focal distances.
Figure 8B:
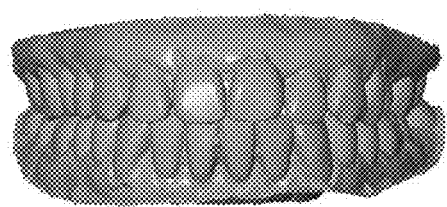

FIGS. 8a and 8b illustrate for example the effect of a modification of the virtual acquisition conditions, in this case of a modification of the focal distance, on the reference image.

The cycling on e2) is continued until the value of the first assessment function indicates that it is decided to exit from this cycling and to continue to the step e3), for example if the score reaches or exceeds said first threshold.

The optimization of the virtual acquisition conditions in the step e2) is preferably performed by using a metaheuristic method, preferably evolutionist, preferably a simulated annealing algorithm. Such an algorithm is well known for nonlinear optimization.

If the cycling was left on the step e2), without a satisfactory score having been able to be obtained, for example without the score having been able to reach said first threshold, the method may be stopped (failure situation) or restarted at the step c) with a new discriminating piece of information and/or with a new updated image. The method may also be continued with the virtual acquisition conditions corresponding to the best score reached. A warning may be emitted in order to inform the user of the error on the result.

If the cycling was left on the step e2) although a satisfactory score was able to be obtained, for example because the score reached, even exceeded, said first threshold, the virtual acquisition conditions correspond substantially to the actual acquisition conditions. Preferably, the virtual acquisition conditions comprise the calibration parameters of the acquisition apparatus. The method conducted thus makes it possible to assess the values of these parameters without it being necessary to know the nature of the acquisition apparatus or its setting. The step b) may therefore be performed with no particular precautions, for example by the patient him or herself by means of his or her mobile phone.

Furthermore, the search for the actual calibration is performed by comparing an updated image with views of an initial reference model in virtual acquisition conditions that are tested. Advantageously, it does not require the updated image to show a standard calibration gauge, that is to say a gauge whose features are precisely known making it possible to determine the calibration of the acquisition apparatus.

WO2006/065955, incorporated for reference, describes the use of images to build three-dimensional models in the field of orthodontic treatments. However, this document does not describe the method that makes it possible to use simple photographs, conventionally presenting partial images of the teeth, blurred image portions and variable glares, taken generally nonsimultaneously, without needing to select noteworthy points on the images, and with an acquisition apparatus whose calibration is unknown.

In a method for monitoring the positioning of teeth according to the invention, the updated images are not used to create a totally new updated three-dimensional model, but only to modify the initial, very accurate, reference model. A totally new updated three-dimensional model created from simple photographs taken with no particular precautions would in particular be too inaccurate for a comparison with the initial reference model to be able to lead to conclusions on the movement of the teeth.

Differences may remain between the virtual acquisition conditions determined and the actual acquisition conditions, particularly if teeth have moved between the steps a) and b). The correlation between the updated and reference images may then be further enhanced by repeating the step e2), the reference model to be tested then being modified by movement of one or more tooth models (step e3)).

The search for the reference model best approximating the positioning of the teeth during the acquisition of the updated image may be performed like the search for the virtual acquisition conditions best approximating the actual acquisition conditions (step e2)).

In particular, the score is assessed by means of a second assessment function. The second assessment function makes it possible to decide whether the cycling on the steps e2) and e3) must be continued or stopped. The second assessment function may for example be equal to 0 if the cycling must be stopped or be equal to 1 if the cycling must continue.

The value of the second assessment function depends preferably on the best score obtained with the reference model to be tested, that is to say on the differences between the updated and reference maps, in the virtual acquisition conditions best approximating said actual acquisition conditions.

The value of the second assessment function may also depend on the best score obtained with one or more reference models tested previously.

For example, it may be decided to continue the cycling if the score does not exceed a second minimum threshold. The value of the second assessment function may also depend on random parameters and/or on the number of cycles of the steps e2) and e3) already performed.

The assessment functions conventionally used in the metaheuristic optimization methods, preferably evolutionist, particularly in the simulated annealing methods, may be used for the second assessment function.

If the value of the second assessment function indicates that it is decided to continue the cycling on the steps e2) and e3), the reference model to be tested is modified and a cycle (steps e2) and e3)) is recommenced with the new reference model to be tested.

The modification of the reference model to be tested corresponds to a movement of one or more tooth models. This modification may be random. The modification is preferably guided by heuristic rules, for example by favoring the modifications which, according to an analysis of the preceding scores obtained, appear most favorable for increasing the score.

Preferably, the movement of a tooth model is sought which has the greatest impact on the score, the reference model to be tested is modified by moving this tooth model, then the cycling is continued on the steps e2) and e3) so as to optimize the score. It is then possible to search, among the other tooth models, for the one which has the greatest impact on the improvement of the score, and once again search for the optimum movement of this other tooth model on the score. This approach may thus be continued with each tooth model.

Next, it is possible to repeat a cycle over the set of the tooth models and to continue thus until a score is obtained that is above the second threshold. Obviously, other strategies may be used to move one or more tooth models in the reference model to be tested and search for the maximum score.

The cycling on the steps e2) and e3) is continued until the value of the second assessment function indicates that it is decided to exit from this cycling and to continue at the step f), for example if the score reaches or exceeds said second threshold.

The search for a reference model with a cycling on the steps e2) and e3) to search for the positions of the tooth models which optimize the score is preferably performed by using a metaheuristic method, preferably evolutionist, preferably a simulated annealing algorithm. Such an algorithm is well known for nonlinear optimization.

If the cycling on the steps e2) and e3) was left without a satisfactory score having been able to be obtained, for example without the score having been able to reach said second threshold, the method may be stopped (failure situation) or restarted at the step c) with a new discriminating piece of information and/or with a new updated image.

If it is decided to restart the method at the step c) from another discriminating piece of information and/or another updated image because the first threshold or the second threshold has not been reached, the choice of the new discriminating information and/or of the new updated image may depend on the scores obtained previously, in order to favor the discriminating information and/or the updated image which, in light of these scores, appear the most promising.

A new discriminating piece of information, obtained for example by the combination of other discriminating pieces of information already tested, may be used. If necessary, there may also be prompting to acquire one or more new updated images. Preferably, indications are provided that make it possible to guide the positioning of the acquisition apparatus for the capture of this new updated image. For example, it is possible to indicate to the patient that he or she should take a photo from the right part of his or her lower arch.

If the cycling on the steps e2) and e3) was left without a satisfactory score having been able to be obtained, the method may also be continued with the reference model and the virtual acquisition conditions corresponding to the best score reached. A warning may be emitted in order to inform the user of the error on the result.

If the cycling on the steps e2) and e3) was left when the satisfactory score was able to obtained, for example because the score reached, even exceeded, said second threshold, the virtual acquisition conditions correspond substantially to the actual acquisition conditions and the tooth models in the reference model obtained (called "final reference model") are substantially in the position of the teeth of the patient at the moment of the step b).

The cycling on the steps e2) and e3) advantageously makes it possible to improve the assessment of the calibration parameters of the acquisition apparatus in the step b).

In the step f), the final reference model, resulting from the optimization by movement of the tooth models, is compared with the initial reference model. The final reference model corresponds substantially to the updated image. The comparison of the step f) therefore makes it possible to observe the differences between the positioning of the teeth in the step a) (initial reference model) and during the acquisition of the updated image (step b)). The method thus makes it possible to determine accurately, for each of the teeth, the movements between these two steps.

By repeating the steps b) and subsequent steps, it is also possible to assess the rate of change of the position of the teeth, and thus to measure, for example, the effectiveness of an orthodontic treatment. A method according to the invention may for example be used to remotely track the evolution of an orthodontic treatment, and thus to minimize the appointments of the patients with their orthodontists.

In a preferred embodiment, the monitoring method according to the invention is implemented several times for a same patient, preferably successively with several discriminating pieces of information, preferably more than 2, more than 3, more than 5 discriminating pieces of information for each updated image and/or with several updated images, preferably more than 2, more than 3, more than 5 updated images. The assessment of the movement of a tooth may thus be refined by taking account of the different scores obtained. The comparison of these scores also makes it possible, if appropriate, to discard the unsatisfactory discriminating pieces of information and/or updated images.

Based on the movement measured, a practical information may be generated. If the movement is small, this practical information may be that no action is to be undertaken. On the other hand, if one or more teeth have moved substantially, the information may be to schedule a visit to the dentist or the orthodontist. Preferably, the practical information depends on the degree of movement of the teeth. In one embodiment, an appointment may be automatically taken with the dentist or the orthodontist, according to the amplitude and/or the nature of the movements detected.

In one embodiment, the practical information is used to modify the time interval after which the patient will have to be alerted that a new updated image must be created.

In one embodiment, the individual apparatus makes it possible to display images, even a sequence of images, showing the positioning of the teeth on different dates. These images may be presented in the form of an animation.

Preferably, the image acquisition apparatus is a telephone which makes it possible to transmit the results obtained by the implementation of the method, preferably securely.

The communication may for example be made, at least partly, wirelessly, preferably according to at least one protocol chosen from the edge, 3 G, 4 G, udmsa, hpdmsa, Bluetooth and Wi-Fi protocols, or by any other protocol, suited to mobile or roaming equipment items, by wired synchronisation with the personal computer, or by optical transmission.

As now emerges, a method according to the invention allows for an accurate and effective monitoring of the positioning of the teeth of the patient, substantially without stress for the patient. In particular, simple photographs taken with no particular precaution, for example with a mobile phone, are sufficient. The patient may therefore easily implement this method.

Obviously, the invention is not limited to the embodiments described above and represented.

In particular, the method is implemented successively for each of the two arches or simultaneously for the two arches.

Furthermore, several different apparatuses may also be implemented. For example, the acquisition may be performed with a mobile phone and the subsequent steps with a fixed computer.

Also, the patient is not limited to a human being. In particular, a method according to the invention may be used for another animal.

Finally, the register mark(s) may be used by the acquisition apparatus to identify a dental situation and/or an action to be achieved by the acquisition apparatus.

The dental situation may in particular be characterized by a pathology and/or an orthodontic treatment and/or a patient and/or said separator and/or another device. The register mark(s) may for instance mean that the separator is intended for a specific pathology, or a for a type of patient, for instance children, or provide the size of the separator, or that the separator should be used in cooperation with another device, for instance should be fixed on a dental imaging device, in particular for implementing a method such as described in international application PCT/EP2015/074896, incorporated by reference. In particular, the dental imaging device may be according to the dental imaging devices disclosed in the patent application filed in the USA on Ser. No. 15/952,635, or US2018303580, incorporated by reference.

In a preferred embodiment, the acquisition apparatus reads the register mark(s) in the updated image, then, depending on the register mark(s), identifies a dental situation and/or an action to be achieved by the acquisition apparatus. Then, the acquisition apparatus acts accordingly. For example, it may provide an information about said dental situation and/or said action, preferably on the screen of the acquisition apparatus. The acquisition apparatus may modify its settings accordingly, for instance the focal distance and/or the exposure time and/or the sensitivity.

In an embodiment, the acquisition apparatus reads the register mark(s), for instance a QR code, in the updated image and finds, in a database, the identification of a pathology and/or an orthodontic treatment and/or a patient and/or a type of separator, for instance a size of the separator. Then, the acquisition apparatus guides the operator of the acquisition apparatus so that he takes a second updated image depending on the identified pathology and/or orthodontic treatment and/or patient and/or type of separator, respectively. For example, if the patient is following an orthodontic treatment which is related to molars, the acquisition apparatus may guide the operator so that he takes one or several second updated images of said molar.

The invention claimed is:

1. A method comprising an acquisition, with an acquisition apparatus, of at least one two-dimensional image of arches of a patient, called updated image, in actual acquisition conditions, a separator separating lips of the patient in order to improve the visibility of patient's teeth, said separator comprising at least three non-aligned register marks,
   wherein the representation of the register mark on the updated image is used to recut the updated image; and/or
   in which relative positions of said at least three non-aligned register marks are measured and trigonometrical computations are achieved to approximately determine the direction from which the updated image has been taken to roughly assess the actual acquisition conditions and/or to guide the positioning of the acquisition apparatus at the moment of the acquisition of the updated image; and/or
   in which the acquisition apparatus
      reads the register marks in the updated image,
      then, depending on the register marks, identifies a dental situation and/or an action to be achieved by the acquisition apparatus,
      then provides an information about said dental situation and/or said action.

2. The method as claimed in claim 1, in which the separator comprises several register marks different according to their position on the separator.

3. The method as claimed in claim 1, in which the register mark is of geometrical shape.

4. The method as claimed in claim 1, in which the register mark is a dot, one or more lines, a star, a circle, an oval, a regular polygon, an image, a letter, a digit or a sequence of letters and/or of digits and/or a QR code and/or a bar code.

5. The method as claimed in claim 1, in which said acquisition apparatus is a mobile phone.

6. The method as claimed in claim 4, in which a reference is presented on a screen of the acquisition apparatus, and the acquisition apparatus is positioned so as to match said reference with said register mark.

7. The method as claimed in claim 6, in which the reference is determined according to the patient and/or a therapeutic treatment for the patient.

8. The method as claimed in claim 1, in which data supplied by the acquisition apparatus are used to roughly assess the actual acquisition conditions.

9. The method as claimed in claim 1, in which
   a focal distance of the acquisition apparatus is assessed with a ratio between a surface area of the register marks on the updated image and a surface area of the updated image and/or
   an exposure time and/or a sensitivity of the acquisition apparatus are assessed from a representation of a register mark on the updated image.

10. The method as claimed in claim 1, in which at least one of said register marks is a relief which does not extend exclusively in a general plane of the separator, and/or in which at least two of said register marks are not in a same frontal plane.

11. The method as claimed in claim 1, in which the separator comprises a relief which takes the form of a tongue which, when the separator is in a service position, extends toward the bottom of the mouth, and in which a representation of said relief is assessed to determine the depth of field of the acquisition apparatus.

12. The method as claimed in claim 1, in which the dental situation is related to a pathology and/or to an orthodontic treatment and/or to said patient and/or to said separator and/or to a device related to the separator.

13. The method as claimed in claim 1, in which the acquisition apparatus, depending on the register mark:
   guides the operator of the acquisition apparatus for the taking of a second updated image, and/or
   modifies its settings.

14. A method for monitoring the positioning of the teeth of a patient, said method comprising:
   a) production of a three-dimensional digital reference model of the arches of the patient, or initial reference model and, for each tooth, definition, from the initial reference model, of a three-dimensional digital reference model of said tooth, or tooth model;
b) acquisition of at least one two-dimensional image of said arches, called updated image, in actual acquisition conditions, a separator comprising at least three register marks separating lips of the patient in order to improve the visibility of patient's teeth,
c) analysis of each updated image and production, for each updated image, of an updated map relating to a discriminating piece of information;
d) optionally, determination, for each updated image, of rough virtual acquisition conditions approximating said actual acquisition conditions;
e) searching, for each updated image, for a final reference model corresponding to the positioning of the teeth during the acquisition of the updated image,
f) for each tooth model, comparison of the positionings of said tooth model in the initial reference model and in the reference model obtained at the end of the preceding steps, called final reference model, in order to determine the movement of the teeth between the steps a) and b),
wherein in step b) and/or in step d), a representation of the register marks on the updated image is used according to claim 1.

15. The method as claimed in claim 14, in which the step e) comprises
a first optimization operation making it possible to search for the virtual acquisition conditions best corresponding to the actual acquisition conditions in a reference model to be tested determined from the initial reference model, and
a second optimization operation making it possible to search, by testing a plurality of said reference models to be tested, for the reference model best corresponding to the positioning of the teeth of the patient during the acquisition of the updated image in the step b).

16. The method as claimed in claim 15, in which a first optimization operation is performed for each test of a reference model to be tested during the second optimization operation.

17. The method as claimed in claim 15, in which the first optimization operation and/or the second optimization operation implement a metaheuristic method.

18. The method as claimed in claim 14 in which the step e) comprises:
e1) definition of the reference model to be tested as being the initial reference model then,
e2) testing of the virtual acquisition conditions with the reference model to be tested in order to finely approximate said actual acquisition conditions, the testing comprising:
e21) determination of virtual acquisition conditions to be tested;
e22) production of a two-dimensional reference image of the reference model to be tested in said virtual acquisition conditions to be tested;
e23) processing of the reference image to produce at least one reference map representing said discriminating piece of information;
e24) comparison of the updated and reference maps so as to determine a value for a first assessment function, said value for the first assessment function depending on the differences between said updated and reference maps and corresponding to a decision to continue or to stop the search for virtual acquisition conditions approximating said actual acquisition conditions with greater accuracy than said virtual acquisition conditions to be tested determined on the last occurrence of the step e21);
e25) if said value for the first assessment function corresponds to a decision to continue said search, modification of the virtual acquisition conditions to be tested, then return to the step e22);
e3) determination of a value for a second assessment function, said value for the second assessment function depending on the differences between the updated and reference maps in the virtual acquisition conditions best approximating said actual acquisition conditions and resulting from the last occurrence of the step e2), said value for the second assessment function corresponding to a decision to continue or to stop the search for a reference model approximating the positioning of the teeth during the acquisition of the updated image with greater accuracy than said reference model to be tested used on the last occurrence of the step e2), and if said value for the second assessment function corresponds to a decision to continue said search, modification of the reference model to be tested by movement of one or more tooth models, then return to the step e2).

19. The method as claimed in claim 14, in which an updated image is acquired less than seven days after the step a), then the steps c) to f) are implemented from this updated image.

20. A method for monitoring the positioning of the teeth of a patient, said method comprising:
a) production of a three-dimensional digital reference model of the arches of the patient, or initial reference model and, for each tooth, definition, from the initial reference model, of a three-dimensional digital reference model of said tooth, or tooth model;
b) acquisition of at least one two-dimensional image of said arches, called updated image, in actual acquisition conditions, a separator comprising a register mark separating lips of the patient in order to improve the visibility of patient's teeth;
c) analysis of each updated image and production, for each updated image, of an updated map relating to a discriminating piece of information;
d) optionally, determination, for each updated image, of rough virtual acquisition conditions approximating said actual acquisition conditions;
e) searching, for each updated image, for a final reference model corresponding to the positioning of the teeth during the acquisition of the updated image; and
f) for each tooth model, comparison of the positionings of said tooth model in the initial reference model and in the reference model obtained at the end of the preceding steps, called final reference model, in order to determine the movement of the teeth between the steps a) and b),
wherein an occlusal plane of the initial reference model is determined according to the following operations:
I. determination of the points of the initial reference model which belong to an arch and which are at a distance from the other arch which is less than a predetermined distance, called points of contact;
II. optionally, filtering of some of the points of contact;
III. linear regression, over all the points of contact remaining so as to determine the occlusal plane.

21. The method as claimed in claim 20, in which the following operations are performed:

i. projection, in an occlusal plane, of the points of contact between the teeth of the upper and lower arches of the patient, according to steps I to III;
ii. determination of the barycenter of the projections of said points of contact and creation of a reference frame, in the occlusal plane, centered on said barycenter;
iii. determination, in said reference frame, of a parabolic function exhibiting the greatest coefficient of correlation with all the projections of said points of contact;
iv. rotation of all the projections of the points of contact about the barycenter, and repeating of the preceding operation iii until all the projections of the points of contact have covered a determined sector;
v. identification of the highest coefficient of correlation for all the angular positions of all the projections of the points of contact about the barycenter, and of the axis of the corresponding parabolic function; and
vi. determination of a median longitudinal plane of the initial reference model, said plane passing through said axis and being at right angles to the occlusal plane.

22. A method for monitoring the positioning of the teeth of a patient, said method comprising:
a) production of a three-dimensional digital reference model of the arches of the patient, or initial reference model and, for each tooth, definition, from the initial reference model, of a three-dimensional digital reference model of said tooth, or tooth model;
b) acquisition of at least one two-dimensional image of said arches, called updated image, in actual acquisition conditions, a separator comprising at least three register marks separating lips of the patient in order to improve the visibility of patient's teeth,
c) analysis of each updated image and production, for each updated image, of an updated map relating to a discriminating piece of information;
d) optionally, determination, for each updated image, of rough virtual acquisition conditions approximating said actual acquisition conditions;
e) searching, for each updated image, for a final reference model corresponding to the positioning of the teeth during the acquisition of the updated image,
f) for each tooth model, comparison of the positionings of said tooth model in the initial reference model and in the reference model obtained at the end of the preceding steps, called final reference model, in order to determine the movement of the teeth between the steps a) and b),
wherein said tooth model is defined according to the following operations:
i'. determination, at least partially, of interior and exterior gingival edges of the arch of the tooth concerned;
ii'. projection, in the occlusal plane, of the interior and exterior gingival edges;
iii'. identification of the deformations of the projections of the interior and exterior gingival edges corresponding to interdental regions, the tops of these deformations being called point of convergence;
iv'. determination of the shortest path, on the surface of the initial reference model, between two points of convergence of interior and exterior gingival edges, respectively, of an interdental region, said shortest path at least partially delimiting a tooth model.

* * * * *